US011578999B2

(12) United States Patent
Isom et al.

(10) Patent No.: US 11,578,999 B2
(45) Date of Patent: Feb. 14, 2023

(54) USAGE TRACKING SYSTEM

(71) Applicant: Counted, LLC, Salt Lake City, UT (US)

(72) Inventors: Michael Osborne Isom, West Valley, UT (US); Duane Michael Scott Johnson, Cottonwood Heights, UT (US); Lance Squire, Salt Lake City, UT (US); Joseph Arthur Harris, Sandy, UT (US); David Brewster Beck, West Jordan, UT (US)

(73) Assignee: Counted, LLC, Salt Lake City, UT (US)

( * ) Notice: Subject to any disclaimer, the term of this patent is extended or adjusted under 35 U.S.C. 154(b) by 667 days.

(21) Appl. No.: 16/418,940

(22) Filed: May 21, 2019

(65) Prior Publication Data

US 2019/0355462 A1 Nov. 21, 2019

Related U.S. Application Data

(60) Provisional application No. 62/674,436, filed on May 21, 2018.

(51) Int. Cl.
*G16H 20/10* (2018.01)
*G01D 5/16* (2006.01)
(Continued)

(52) U.S. Cl.
CPC ............... *G01D 5/24* (2013.01); *A61J 1/035* (2013.01); *A61J 7/0076* (2013.01); *G01D 5/16* (2013.01);
(Continued)

(58) Field of Classification Search
CPC ........ A61J 1/035; A61J 7/0076; A61J 7/0436; A61J 220/30; G01D 5/16; G01D 5/24; G16H 10/20; G16H 20/10
See application file for complete search history.

(56) References Cited

U.S. PATENT DOCUMENTS

| 5,412,372 A * | 5/1995 | Parkhurst | A61J 7/0481 340/568.1 |
| 7,178,417 B2 * | 2/2007 | Petersen | A61J 7/0481 73/865.8 |

(Continued)

OTHER PUBLICATIONS

PCT Application No. PCT/US2019/033415 International Search Report and Written Opinion dated Aug. 22, 2019.

*Primary Examiner* — Gene O Crawford
*Assistant Examiner* — Kelvin L Randall, Jr.
(74) *Attorney, Agent, or Firm* — Greenberg Traurig (57) ABSTRACT

Embodiments are generally directed to systems and apparatuses for tracking usage of an item. For example, an apparatus may be provided for tracking use of a packetized item. The apparatus may include a microprocessor, a power source, and a structural layer to which the microprocessor and power source are coupled. The structural layer may include a container that is configured to hold various items. The container may also include an opening that allows access to the items. The apparatus may further include a cover layer that is configured to cover the opening of the container. The cover layer may include at least one bendable sensor placed over the opening of the container. The microprocessor may be configured to determine, using detected movements in the bendable sensor, whether the container has been opened.

19 Claims, 6 Drawing Sheets

(51) Int. Cl.
  *G01D 5/24* (2006.01)
  *G16H 10/20* (2018.01)
  *A61J 1/03* (2006.01)
  *A61J 7/00* (2006.01)

(52) U.S. Cl.
  CPC ............ *G16H 10/20* (2018.01); *G16H 20/10* (2018.01); *A61J 2200/30* (2013.01)

(56) References Cited

U.S. PATENT DOCUMENTS

| | | | |
|---|---|---|---|
| 8,120,492 B2 * | 2/2012 | Scharfeld | G08B 13/2417 340/572.7 |
| 8,960,440 B1 * | 2/2015 | Kronberg | A61J 1/035 206/531 |
| 10,013,534 B2 * | 7/2018 | Blochet | A61J 7/04 |
| 10,083,594 B2 * | 9/2018 | Mehregany | A61J 7/0436 |
| 10,185,811 B2 * | 1/2019 | Dixit | G16Z 99/00 |
| 10,561,581 B2 * | 2/2020 | Wong | A61J 7/02 |
| 2005/0241983 A1 * | 11/2005 | Snyder | A61J 7/0481 206/539 |
| 2008/0053040 A1 * | 3/2008 | Petersen | H05K 1/0293 53/396 |
| 2008/0054007 A1 | 3/2008 | Mador | |
| 2009/0001988 A1 | 1/2009 | Allison et al. | |
| 2013/0285681 A1 * | 10/2013 | Wilson | A61J 1/035 324/693 |
| 2016/0132661 A1 * | 5/2016 | Dixit | G16H 20/13 206/531 |
| 2017/0053200 A1 | 2/2017 | Bright | |
| 2017/0248401 A1 * | 8/2017 | Isom | A61J 7/0481 |

* cited by examiner

USAGE TRACKING SYSTEM

CROSS-REFERENCE TO RELATED APPLICATIONS

This application claims priority to and the benefit of U.S. Provisional Application No. 62/674,436, entitled "Usage Tracking System," filed on May 21, 2018, the entirety of which is incorporated by reference herein.

BACKGROUND

Many items that are produced are never opened. And many items that are produced for a certain individual are opened by the wrong individual. Still further, there is no way to track usage of a wide variety of products that are purchased and sold throughout the country. Providers of these goods may wish to know whether their goods end up being used and, if so, how they are used. This is especially true for pharmaceutical manufacturers, and producers of medical supplies and devices. Currently, there is no reliable mechanism for tracking such use.

BRIEF SUMMARY

Embodiments described herein are directed to systems and apparatuses for tracking usage of an item. In one embodiment, an apparatus is provided for tracking use of a packetized item. The apparatus includes a microprocessor, a power source, and a structural layer to which the microprocessor and power source are coupled. The structural layer may include a container that is configured to hold various items. The container may also include an opening that allows access to the items. The apparatus may also include a cover layer that is configured to cover the opening of the container. The cover layer may include at least one bendable sensor placed over the opening of the container. The microprocessor may be configured to determine, using detected movements in the bendable sensor, whether the container has been opened.

In some examples, the apparatus may further include a transmitter configured to transmit data from the apparatus to a target destination. In some examples, the structural layer may include multiple different capsules for storing items. Each capsule may have its own opening and a bendable sensor extending over at least a portion of the opening.

In some examples, the bendable sensor may include one or more traces. In some cases, these traces may be generated and applied using printable ink. In some examples, the traces of the bendable sensors may remain intact even when the container of the structural layer has been opened. In some examples, at least some portion of current continues to flow through the bendable sensor even after the container has been opened.

In some examples, the microprocessor may determine whether the container has been opened using detected movements in the bendable sensor by detecting changes in capacitance, resistance, current, and/or voltage through the bendable sensor. In some examples, the changes in capacitance, resistance, current, and/or voltage through the bendable sensor may be detected by the microcontroller without breaking the bendable sensor. As such, the detected amounts of capacitance, resistance, current, or voltage are non-zero values, even if the container has been opened.

In some examples, a system may be provided for tracking usage of an item. The system may include a microprocessor, a power source, and a structural layer to which the microprocessor and power source are coupled. The structural layer may include at least one container that is configured to hold an item. The container may also include an opening that allows access to the item. The system may also include a cover layer configured to cover the opening of the container. The cover layer may include at least one bendable sensor placed over the opening of the container. The microprocessor may be configured to determine, using detected movements in the bendable sensor, whether the container has been opened.

In some examples, the structural layer and the cover layer may be combined into a single layer. In some examples, the system may include the structural layer, the cover layer, and a further sensor layer. In some examples, the structural layer may comprise a backing layer, the cover layer may comprise a lidding foil and a sensor lidding foil, and the system may further include a blister layer, a blister lidding, a dielectric layer, and a sensor layer.

In some examples, the microprocessor may be configured to continually monitor a state associated with various traces of the bendable sensor at a periodic rate. In some examples, the microprocessor may be configured to determine whether the container has been opened, when the container was opened, and where the container was when the container was opened. In some examples, the structural layer may include multiple containers. In such examples, the microprocessor may be configured to determine if a specified container is opened, even out of order in relation to the other containers.

In some examples, the system may further include a camera and microphone communicatively connected to the microprocessor. In some examples, the system may further include a display configured to display various images, words, or videos. In some examples, the display may include an interactive interface that is configured to present a question to the patient asking if the patient is experiencing various negative side effects. If so, the patient's doctor may take certain actions with respect to the patient's prescription.

In some examples, a method of manufacturing may be provided. The method of manufacturing may include providing a structural layer to which a microprocessor and a power source are coupled. The structural layer may include a container that is configured to hold at least one item. The container may include an opening that allows access to the item. The method of manufacturing may also include adhering a cover layer to the structural layer. The cover layer may be configured to cover the opening of the container. The cover layer may include at least one bendable sensor placed over the opening of the container. The microprocessor may be configured to determine, using detected movements in the bendable sensor, whether the container has been opened.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be apparent to one of ordinary skill in the art from the description or may be learned by the practice of the teachings herein. Features and advantages of embodiments described herein may be realized and obtained by means of the instruments and combinations particularly pointed out in the appended claims. Features of the embodiments described herein will become more fully apparent from the following description and appended claims.

BRIEF DESCRIPTION OF THE DRAWINGS

To further clarify the above and other features of the embodiments described herein, a more particular description will be rendered by reference to the appended drawings. It is appreciated that these drawings depict only examples of the embodiments described herein and are therefore not to be considered limiting of its scope. The embodiments will be described and explained with additional specificity and detail through the use of the accompanying drawings in which.

DETAILED DESCRIPTION

Embodiments described herein are directed to systems and apparatuses for tracking usage of an item. In one embodiment, an apparatus is provided for tracking use of a packetized item. The apparatus includes a microprocessor, a power source, and a structural layer to which the microprocessor and power source are coupled. The structural layer may include a container that is configured to hold various items. The container may also include an opening that allows access to the items. The apparatus may also include a cover layer that is configured to cover the opening of the container. The cover layer may include at least one bendable sensor placed over the opening of the container. The microprocessor may be configured to determine, using detected movements in the bendable sensor, whether the container has been opened The embodiments described herein may implement various types of microprocessors, microcontrollers or computing systems. These computing systems are now increasingly taking a wide variety of forms, including embedded computing systems, mobile computing systems (e.g., smartphones), wearable computing systems (e.g., smart watches), or other types of computing systems. As used herein, the term "computing system" includes any device, system, or combination thereof that includes at least one microprocessor, and a physical and tangible computer-readable memory (e.g. EEPROM or Flash memory) capable of having thereon computer-executable instructions that are executable by the processor.

The apparatuses and systems described herein can include a plurality of independent components that each contribute to the functionality of the system as a whole. This modularity allows for increased flexibility when approaching issues of platform scalability and, to this end, provides a variety of advantages. System complexity and growth can be managed more easily through the use of smaller-scale parts with limited functional scope. Platform fault tolerance is enhanced through the use of these loosely coupled modules. Individual components can be grown incrementally as business needs dictate. Modular development also translates to decreased time to market for new functionality. New functionality can be added or subtracted without impacting the core system.

Figure 1:
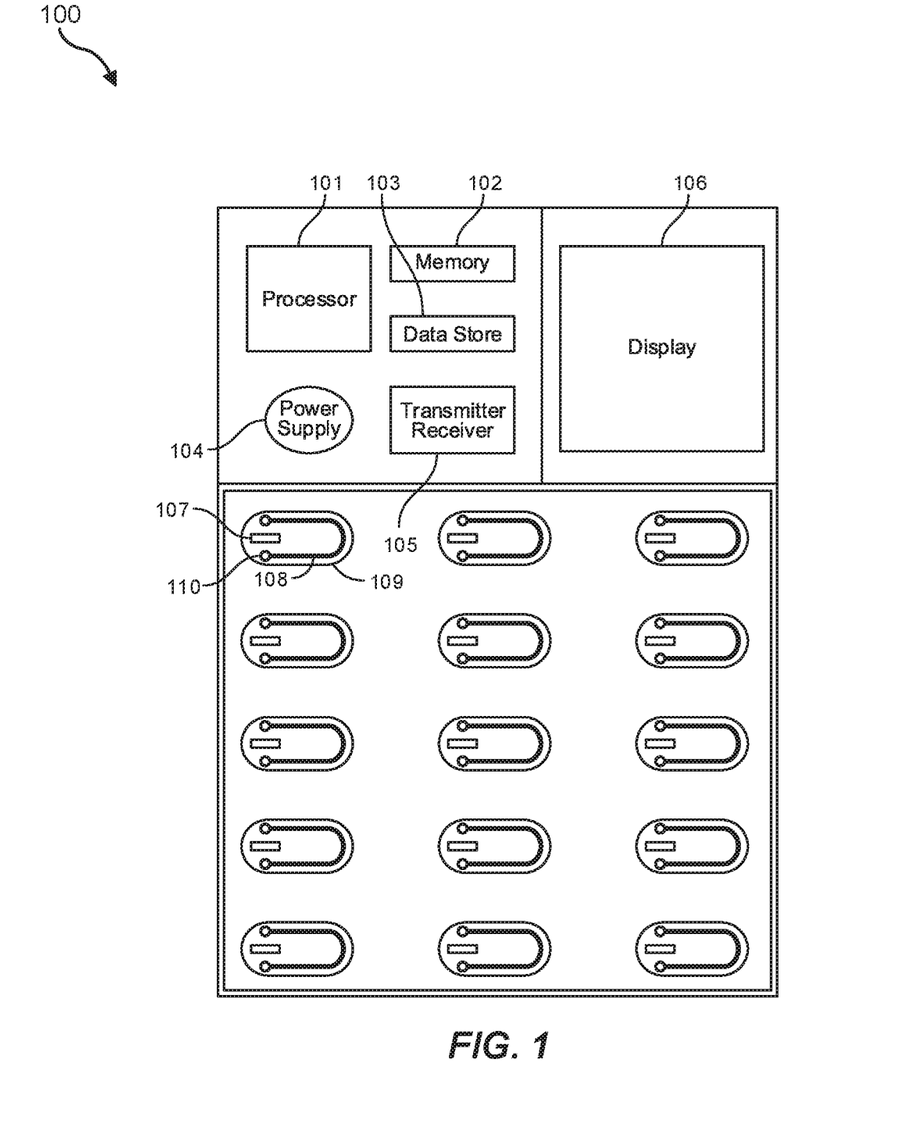
FIG. 1 illustrates an embodiment of an apparatus for tracking usage of an item.

FIG. 1 illustrates a schematic diagram of an apparatus 100 for tracking usage of an item. The item that is to be tracked may be substantially any item that can be held in a container. For example, the various containers 109 of FIG. 1 may be designed to hold pills or other controlled substances. Each container 109 may include one or more such pills. The containers may have sensors placed thereon that are configured to detect when a container has been opened, either fully or partially. For example, a bendable sensor 107 may be placed over the lid 108. The lid 108 may be configured to bend at a position 110 over the contained item. As will be explained further below, the bendable sensor 107 may detect changes to the lid 109. These changes may include a range of different measurements include fully closed, partially open, fully open, or other intermediate measurements.

To track the contained items, traces may be printed or otherwise placed over the item directly. For example, bendable sensors 107, which may include printed traces, may be placed over the opening of each container. In FIG. 1, for example, bendable sensors 107 may be placed over each of the capsules in a blister pack of capsules. It should be recognized here that although blister packs are described herein and shown in the Figures, the bendable sensors described may be applied in a wide variety of different scenarios, including on different types of apparatuses, and in different environments.

The containers described herein may be designed to hold pharmaceuticals, for example, or other items for which usage tracking is desirable. For instance, the containers may be shaped and sized to hold syringes, medical instruments, or other medical supplies. In other embodiments, the containers may be designed to hold personal valuables, or collectable items such as baseball cards, comic books, signed memorabilia, or other items that are to remain sealed. In FIG. 1, the containers 109 may include many different capsules arranged in rows. By applying the tracking systems described herein, a hospital or pharmaceutical manufacturer or home user (or other entity) can track the containers and determine when the containers have been opened. The bendable sensors 107 may be configured to detect when a container has been opened without breaking a trace or without detecting an open or short circuit.

The apparatus 100 may include various electronic components, each of which may contribute to the apparatus' ability to track the usage of different items. For example, the apparatus 100 may include a processor 101. The processor 101 may include substantially any type of processing chip including a generic central processing unit (CPU), an application-specific integrated circuit (ASIC), a field-programmable gate array (FPGA), a digital signal processor (DSP), or other similar stand-alone chip configured to process data inputs in a specified manner. The processor 101 may be a silicon-based integrated circuit having computer-executable logic stored thereon that is designed to perform one or more specified tasks. Additionally or alternatively, the computer-executable logic may be stored in memory 102 or in a data store 103. The data store 103 may include any type of non-volatile memory, while memory 102 may include any type of volatile memory.

The processor 101 may work in conjunction with the memory 102 and the data store 103 to process computer-executable code including instructions that cause the processor to track the usage of items stored in containers 109, for example. The processor and other electronic components may be powered by a power supply 104. The power supply may be a battery, solar cell, wired power supply, or other type of power supply. The apparatus 100 may also include a transmitter, receiver, or transceiver 105. The transceiver 105 may be configured to transmit data and/or receive data to or from other entities. The transceiver may be a radio such as a WiFi radio, a Bluetooth radio, a cellular radio, a radio frequency identifier (RFID), a global positioning system (GPS) radio, or other type of radio. In some cases, the apparatus 100 may have multiple radios including an RFID chip that identifies the apparatus among a plurality of other apparatuses, a WiFi radio to communicate status updates to nearby WiFi routers, and a GPS radio to identify the location of the apparatus 100.

Still further, the apparatus 100 may include a display 106. The display 106 may be configured to show a wide variety of different data including information related to a patient, information related to a prescription, information related to dosage, pill reminder messages, live video streams from doctors or nurses, or other types of information. The display 106 may be configured to display information received via transceiver 105. The display 106 may also be configured to display information related to the user's usage of the items in the various containers 109.

Each container 109 may have one or more bendable sensors 107 placed over some or all of the opening to the container. The bendable sensors 107 may include substantially any type of sensor configured to detect movement, displacement, or opening of a container 109 or container lid or covering 108. These movements or changes may be determined by a microcontroller or processor 101 which may sample the bendable sensors 107 at various time intervals to detect changes. These changes may include changes in resistance, changes in capacitance, or changes in voltage or current. By using these bendable sensors, the microcontroller may not need to determine whether a trace in the sensor has been broken, which would result in an open circuit. Rather, the traces in the bendable sensors may remain intact, allowing current to flow, even when the container has been opened. Such traces may be more reliable, more robust, and more likely to provide accurate results.

Figure 2A:
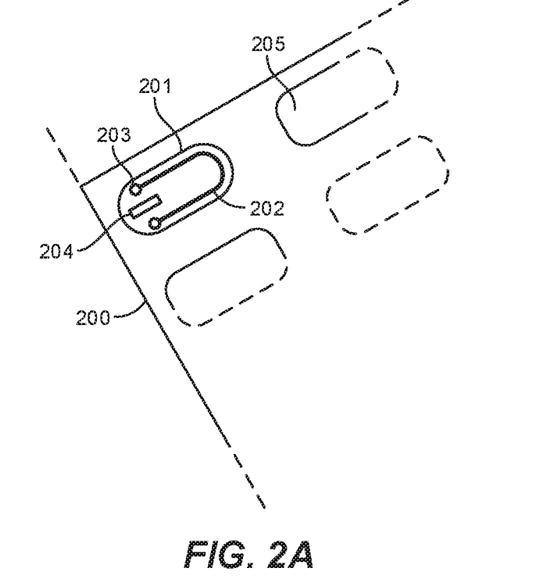
FIGS. 2A-2C illustrate embodiment of an apparatus for tracking usage of an item in various stages of opening.

The bendable traces 107 may detect movement in a variety of positions. For example, as shown in FIG. 2A, an apparatus 200 may include many different containers 201, 205, etc. Each container may have one or more bendable traces 204 placed thereon or printed thereon. The bendable traces 204 may be designed to detect movement of a lid or moveable portion 202. The lid 202 may be configured to deform or bend upon being pushed or pulled by a user. The lid may bend at designed points 203. In some cases, these points 203 may be further forward or back relative to the sensor 204. This may allow the bendable sensor 204 to detect larger or smaller movements of the lid.

Figure 2B:
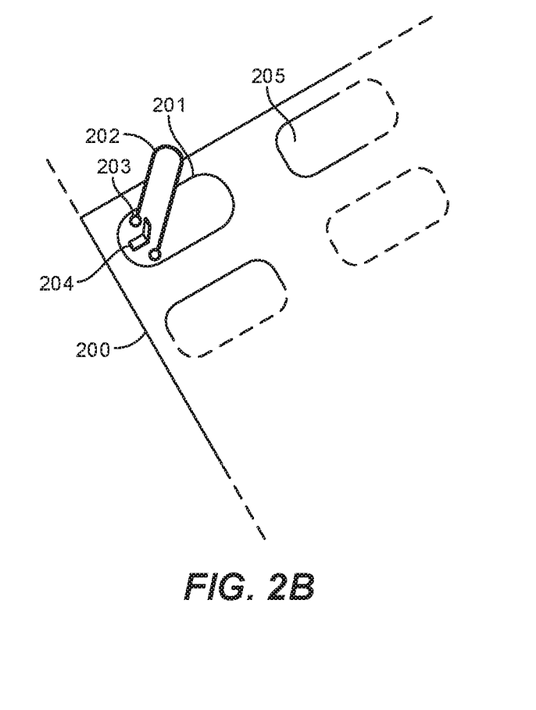
Figure 2C:
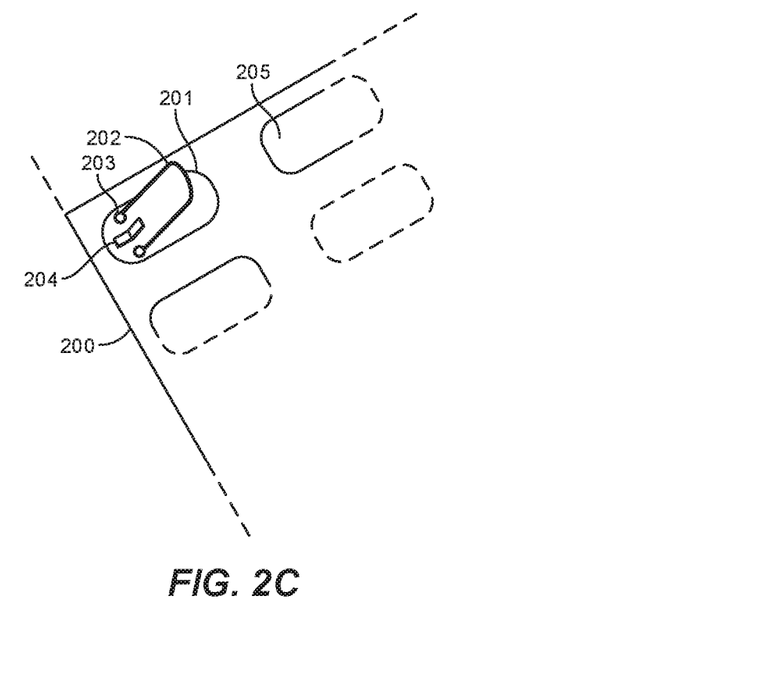

In some cases, as shown in FIG. 2B, the lid 202 may be pulled back to a fully open position. In such cases, the bendable sensor 204 is bent upward near the designed points of flexure. In other cases, as shown in FIG. 2C, the bendable sensor may be pulled back to a partially open position. In such cases, the bendable sensor may be bent upward, but may not be bent as far as a fully open lid as in FIG. 2B. Thus, the bendable sensor 204 may report a wide variety of different levels of openness. For example, the lid may be 0 degrees open in FIG. 2A, 90 degrees open in FIG. 2B, 45 degrees open in FIG. 2C, or some other degree open (e.g., 10 degrees or 110 degrees). This may provide useful information to an item manufacturer. For instance, a lid that was only open 10 degrees may likely still contain the item. If, for example, the item would not fit out of a lid that was only open 10 degrees, then even though the lid has been slightly opened, the item may still be presumed to be inside the container. If, on the other hand, the container has been fully opened (e.g., 90+ degrees), the item may be presumed to have been removed. Thus, the bendable sensors may report a very fine-grained level of openness for each container in the apparatus 200.

Figure 3:
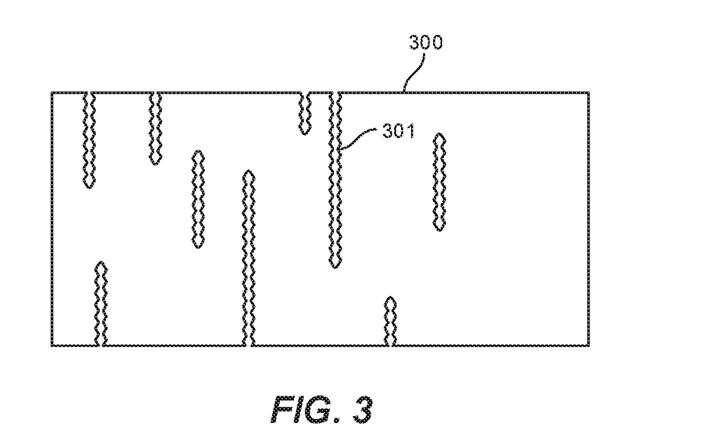
FIG. 3 illustrates an embodiment of a close-up view of a trace on a bend sensor that has been damaged due to bending.

FIG. 3 illustrates an embodiment of a bendable sensor 300. The bendable sensor 300 may include one or more electronic traces capable of carrying an electric charge. (While the embodiment shown in FIG. 3 only includes a single trace, it will be understood that each bendable sensor may include multiple traces laid out in rows, columns, or in other patterns). When the bendable sensor 300 is bent or deformed, the traces may sustain microscopic cracks 301. These cracks 301 may result in a step-function increase in detectable resistance. This increase in resistance may be detected by the processor or microcontroller 101 of FIG. 1. If a threshold amount of change occurs, the microcontroller may determine that a container has been opened or has been opened some amount. If smaller changes occur, the microcontroller may determine that the packaging has been twisted or tampered with, but not opened or only slightly opened. This information may also be passed on to appropriate parties using the transmitter 105.

Figure 4:
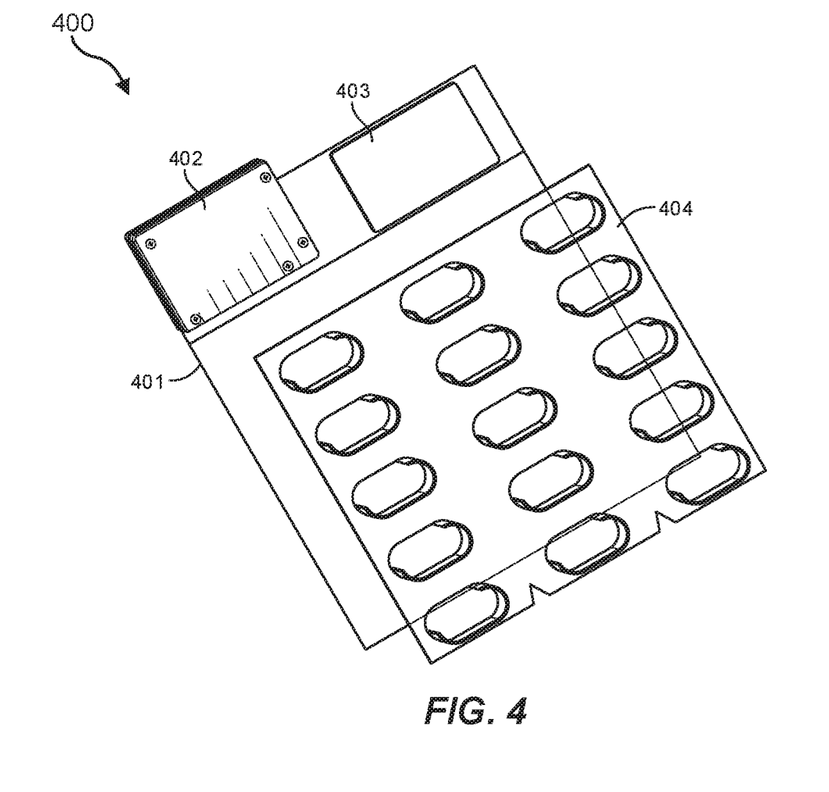
FIG. 4 illustrates an alternative embodiment of an apparatus for tracking usage of an item.

FIG. 4 illustrates an embodiment 400 in which a blister pack 404 is applied to a structural layer 401. In this embodiment 400, a detachable, reusable signal processing board or "dock" 402 may be attached and/or detached. The dock 402 may include a power supply (e.g. a battery), a microprocessor, electrical traces attaching the microprocessor to the bendable sensors, and in some cases, a transmitter and/or a display 403. This signal processing board 402 or electronics board may be attached to a given blister pack 404 and may be used with that pack until some or all of the blister packs have been opened. Once the blister packs are empty or are no longer going to be used, the electronics board may be detached and attached to a new or different blister pack.

In some embodiments, the components of the electronics board 402 may be embedded into the tracking apparatus itself (400), such that the entire apparatus is disposable and is only used once. In other cases, the electronics board 402 may be detachable and may be reusable with other blister packs (or other tracking apparatuses depending on which type of tracking apparatus is used). In such cases, the structural layer 401 with the blister pack 404 may be a separate item that may be detached from the dock 402. The combined structural layer 401 and blister pack 404 may have electrical connectors that slide into the dock 402 and interface with the microprocessor and/or other electrical components of the dock. In some cases, when the combined structural layer 401 and blister pack 404 are inserted into the dock 402, the microprocessor may register an event. This even may note the current time and location of the apparatus 400. A similar event may be created when a combined structural layer 401 and blister pack 404 is removed from the dock 402.

In some embodiments, the dock 402 may be configured to report data including these events to one or more user or entities. These entities may run software applications configured to interpret and display the data and events received from the dock 402 (and other docks for other item tracking devices). The software applications may display maps showing markers indicating where and when events have occurred. The events may include a combined structural layer 401 and blister pack 404 being inserted or removed from a dock, a pill container being opened, a user input being received through the dock's touchscreen display, or other events. Using this map, a user or entity (e.g., a healthcare provider or family member) may see where and when pill blister packs are being used.

In some embodiments, the location information for a given item tracking apparatus 400 may or not be tracked according to policy. For example, a healthcare entity may establish a geofence within which item tracking apparatuses are to be tracked. For instance, a hospital may establish a geofence around its boundaries and track all events within that geofence. The dock 402 may use its radios to establish its location and, if within the geofence, report its events. If the dock determines that it is outside of this established geofence, it may store its events locally but may not report them to the healthcare provider. In other cases, policies may dictate that the location information is to be reported regardless of geofences (e.g., if the patient has been particularly loath to take their medication). In still other cases, the location may only be reported if too many pill containers are opened within a specified amount of time (e.g., within a day). Thus, healthcare providers or other users may be able to establish policies that control which data is reported and when that data is reported.

Each combined structural layer 401 and blister pack 404 may have its own identifier, and each dock 402 may have its own identifier. Still further, the prescription given to the patient may also have its own identifier. In some cases, the board ID, the dock ID, and/or the prescription ID may each be encrypted. The drug manufacturer may know the board ID and the dock ID, but may not know the prescription ID. The pharmacy may know the board ID, the dock ID, and the prescription ID so that when they assign a prescription ID to a given board and dock, they will know which pills were given to which patient and where that patient's pills were when they were opened. Accordingly, pharmacies, healthcare providers, or other users privy to a patient's pill use may receive information indicating which blister pack was inserted into which dock, when that insertion occurred, which pills were taken (or at least opened), what time the pill containers were opened, and where the containers were opened. This information may be used to encourage proper consumption of medication and prevent the misuse of prescription drugs.

Figure 5:
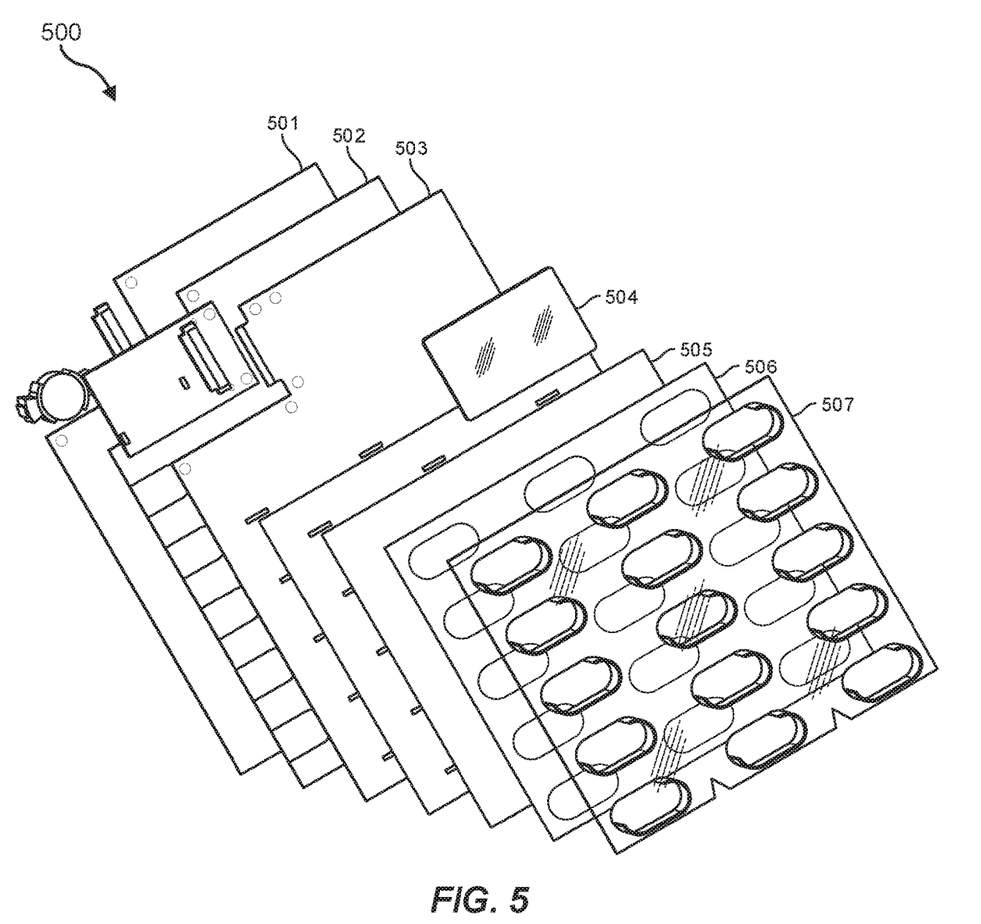
FIG. 5 illustrates an alternative embodiment of an apparatus for tracking usage of an item.

As shown in FIG. 5, one embodiment of a tracking apparatus 500 may be arranged as a blister pack that includes a plurality of layers. The layers may include, from top to bottom, a blister layer (507), a blister lidding (506), a lidding foil (505), a sensor lidding foil (504), a dielectric layer (503), a sensor layer (502) and a backing layer (501). Although many layers are shown in FIG. 5, it will be recognized that more or fewer layers may be used. For example, in some embodiments, the tracking apparatus (e.g., 100 of FIG. 1) may be constructed using three layers: a conductive layer (e.g. a lidding foil layer), a sensor layer that includes ink traces (e.g. bendable sensors 107), and a structural layer (e.g. cardboard).

Each of these three layers or each of the seven layer of apparatus 500 of FIG. 5 may be adhered to one another using some type of non-conductive adhesive. These layers may be constructed in different orders or arrangements, and may include a single layer that combines structure, sensing and conducting, or other layers that perform one or all of these functions. In some embodiments, the bendable sensors may be printed on the back of the lidding foil (or other conductive layers) and then laminated or otherwise bonded to a structural layer. In such cases, the lidding foil and sensors may be separated by a dielectric layer. Many other such permutations and configurations are possible.

The bendable sensors (e.g., 107 of FIG. 1 or 204 of FIG. 2A) may include any of the sensor embodiments described in U.S. Pat. No. 7,277,004, which patent, including all of its description and drawings, is incorporated herein by reference. The traces of the bendable sensors may be connected to a power source and a microcontroller or microprocessor (e.g., 101 of FIG. 1). The microcontroller 101 may monitor resistance changes, capacitance changes, voltage changes, or some other electrical characteristic in each trace or bendable sensor. The monitoring may be continuous or may occur at specified intervals. For instance, the microcontroller may poll the traces every second, every minute, every 10 minutes, etc., to determine whether resistance, capacitance, or other measurements have changed for each trace. In some embodiments, each trace or sensor may be individually tracked, while in other cases, the traces may be tracked in regions or groups. For instance, the microcontroller may track the status of a given row or set of rows of blister containers. Thus, at each polling period, the microcontroller can determine which sensors have been bent, how far those sensors were bent, and may thus identify which items have been opened, either fully or partially.

In one example, if the traces are affixed or printed on a tray of pharmaceutical pills, the traces may be bent or pushed out of their normal position when the pills are pushed out of their capsules. The traces printed over the capsules may have been bent, resulting in small cracks in the trace ink (e.g., as shown in FIG. 3). These traces may now exhibit a change in relative resistance or capacitance. For example, the traces may have an initial resistance level of approximately 900 Ohms, and after the bending, may have a resistance level of approximately 200-300 Ohms. Using this information, the microcontroller (e.g., 101 of FIG. 1) may determine, at each polling period, which traces have experienced changes in resistance, and which have not. This then may indicate which pills have been dispensed and which pills still remain in the blister pack. The microcontroller may further determine when each pill was pushed out. For instance, if the microcontroller is continually monitoring the state of the traces, the microcontroller may reference an internal clock indicating when each pill was dispensed. If the microcontroller is monitoring the state of the traces every five minutes, for example, the microcontroller may determine, within a five-minute window, which pills were dispensed.

In some embodiments, the microcontroller may be connected to a single tray of pills. In other embodiments, the microcontroller may be connected to multiple different trays of capsules. Each tray may have its own identifier. This identifier may be physically printed on the tray and/or may be an electronic identifier that may be stored in memory. This memory may be read by the microcontroller and, as such, the identity of the tray can be determined. A signal generator may generate trace signals continuously, or at a specified rate, and when the signals from the generator travel through the traces, the signals may travel through or over each capsule individually. Thus, if a capsule lid is bent, regardless of where the capsule is positioned within the rows of capsules (e.g., even out of order), the microcontroller may be configured to determine which exact capsule was opened and when.

As noted above, the apparatus may include one or more transmitters, as well as one or more receivers or transceivers. These communication components may include hardware radios such as WiFi radios, GPS radios, Bluetooth radios, RFID radios, Cellular radios or other types of communication hardware. The radios may be used to transfer data between the apparatus and outside computing systems (such as cloud data stores or other databases). The radios may also be used to determine the location of the apparatus. For example, at each polling, the microcontroller may communicate with one or more of the radios to determine the current location of the apparatus (e.g., using GPS and/or WiFi signals). Thus, information generated at each polling may include an indication of which traces have been bent, and which are still connected, the time of the polling, and the location of the apparatus. Each of these pieces of information may be useful in determining how, where, and when pharmaceuticals (or other packaged items) are dispensed from the packaging. This information may also be used to determine which pharmaceuticals are still in the containers. As such, a remote party (e.g., a remote doctor, nurse, or caregiver) may be able to determine which pills have been taken and which remain in the package.

The traces in the bendable sensors shown in the apparatus 100 of FIG. 1 may also be applied in other situations to track usage of an item. For example, traces may be printed on or otherwise applied to the seal of an envelope or other packaging item such as a box or sealed container. The packaging item may include an embedded battery, microcontroller, traces and/or a radio. The traces may be applied to the packaging item over one or more seals, such that upon opening of the seal, at least one of the trace connections is bent, and the packaging item is determined to have been opened. In this manner, companies could track which packages or envelopes are actually opened and which are not opened. Moreover, the apparatus could indicate when and where the packaging item was opened. Similar traces could be applied to pill bottles or other containers whose open or closed state is desirable to track.

At specified periods, the microcontroller may generate an indication of the type of usage that occurred and the time it occurred. This indication may then be transmitted to one or more specified recipients (e.g. users and/or databases). The indication of usage may also include an indication of where the item was when each usage occurred as well as provide an identifier for the apparatus and/or the identifier of the blister pack. This indication may be sent at specified intervals, or at certain times. The indications may be stored in a database. The database may be a local database or a distributed data store such as a cloud database.

The tracking apparatus may be configured to operate as a standalone device, or maybe contained within a container or case. In some embodiments, the tracking apparatus may include an electronic display. The electronic display may provide information related to the blister pack and/or to its intended user. The display itself may be a liquid crystal display (LCD), electrophoretic display, or other type of electronic display. The display may indicate, among other things, whether the user has taken their medication. Indicators in the display may show whether the user has complied with their prescription that day. If a user has not complied with their daily prescription, a further indication may be provided on the display, such as a colored light, to remind the user the current state of their compliance that day. The display may show the user's name, the medication they are taking, a battery level, and other data.

For example, the display may show dynamic changes in the user's health record (e.g. an electronic health record (EHR)). If a doctor notes a change in the patient's condition and makes a change to his or her medication, the display may be updated to show new dosage information, or changes to how the prescribed drug is to be administered. The tracking apparatus may have buttons that allow users to interact with internal or external applications. For instance, point of care questions may be asked to a person using the dock, and the user may respond using one of these buttons to indicate a yes answer or button to indicate a no answer. Answers to such questions may provide additional insight to the doctor or nurse that may cause the medication dosage or method of administering the drug to be changed.

For example, some drugs may have negative side effects. The display on the tracking apparatus may present a question to the patient asking if they are experiencing a specific negative side effect. If yes, the doctor may take certain actions with respect to the patient's prescription. Other buttons or forms of interaction may also be provided on the dock. For instance, the display may be a touchscreen, or may allow voice or video interaction with a doctor using a built-in camera and microphone. Data provided through the touchscreen, buttons or other interfaces may be transmitted using the transceiver of the device.

Figure 6:
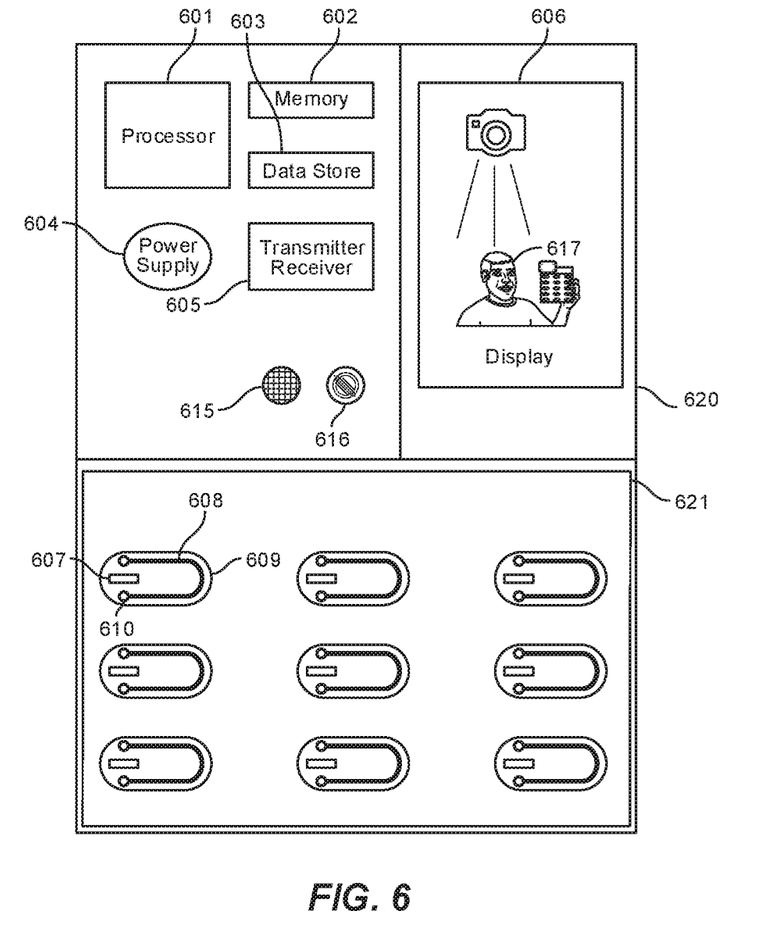
FIG. 6 illustrates an alternative embodiment of an apparatus for tracking usage of an item.

FIG. 6 illustrates an embodiment of a system 600 for tracking usage of an item. The system may include a microprocessor 601, a power source 604, and a structural layer 620 to which the microprocessor and power source (along with at least some of the other electronic components) are coupled. The structural layer 620 may include a container 609 (or multiple containers) that is configured to hold various items. The container 609 may also include an opening or lid 608 for each item that allows access to the item. The system 600 may also include a cover layer 621 that is configured to cover the opening or lid 608 of the container 609. The cover layer 621 may include at least one bendable sensor 607 placed over the opening of the container. The microprocessor 601 may be configured to determine, using detected movements in the bendable sensor, whether the container has been opened.

The system 600 may also include a transmitter and/or receiver 605 that may be configured to transmit data from the system to a target destination or entity. Other electronic components may include volatile memory 602, non-volatile memory 603, a microphone 615, a camera 616, and a display 606. The structural layer 620 may provide support for any or all of these electronic components. In some embodiments, the structural layer 620 and the cover layer 621 may be combined into a single layer. These two layers may be glued together or otherwise bonded such that the two layers (620 and 621) effectively become one layer. In some cases, as noted in FIG. 5, the system may further include other layers including a backing layer, a blister layer, a blister lidding, a dielectric layer, and a sensor layer. In such cases, the cover layer may include a lidding foil and a sensor lidding foil. Each of these layers may form a structure that links electronic components to bendable sensors, such that the structure may track usage of items.

Each item that is to be tracked may be placed in a container or capsule. Each capsule may have its own opening and a bendable sensor extending over at least a portion of the opening. For example, in FIG. 6, each container 609 may include a bendable sensor 607 placed over at least a portion of the opening 608. In some cases, as noted above, the bendable sensor 607 may include one or more traces. These traces may be generated and applied using printable ink. In other cases, the traces may be applied using etching and filling or other method of manufacturing traces. In examples where the traces are applied using printable trace material, the printable trace material may be specifically formulated to bend repeatedly and still conduct electricity.

When a user opens a container (e.g., 609), the traces of the bendable sensors 607 may remain intact even when the opening or lid 608 of the structural layer has been opened. Indeed, even if a user has punctured and opened a capsule by peeling back the lid 608, at least some portion of current may continue to flow through the bendable sensor. Alternatively, the processor 601 may be configured to detect resistance through the bendable sensor 607. The bendable sensor 607 may have an initial resistance value which may be reduced when the sensor is bent due to the microscopic cracks created by the bending. This change in resistance may not rise to infinite as it would in an open circuit. Rather, the change in resistance may be gradual, or may be within a defined threshold. Similarly, the change in current flow, voltage, capacitance, or other measure of an electrical characteristic may change within known thresholds. Thus, these electrical characteristics may not drop to zero or rise to infinity as they would in a short circuit or open circuit; rather, the bendable sensory may detect changes along a known scale.

Thus, the microprocessor 601 may determine whether the container has been opened using detected movements in the bendable sensor 607 by detecting changes in capacitance, resistance, current, and/or voltage through the bendable sensor. These changes in capacitance, resistance, current, and/or voltage through the bendable sensor may be detected by the microcontroller 601 without breaking the bendable sensor 607. As such, the detected amounts of capacitance, resistance, current, or voltage may be non-zero values, even if the container has been opened. Still further, depending on the size of the contained object (e.g., a pill or syringe or envelope or signed baseball card), the microcontroller 601 may determine whether the opening in the lid 608 was sufficient to remove the item from the container. If the microcontroller 601 determines that, although the lid 608 was opened to a degree, the opening was insufficient to remove the item (based on pre-specified parameters) based on the size of the item and the size of the opening, the microcontroller may indicate that the item is still in the container. If, however, the bendable sensor has bent far enough to indicate an opening large enough to allow the item to be pulled free, the microcontroller 601 may indicate that the item has been removed from the container 609.

In some embodiments, the microprocessor 601 may be configured to continually monitor a state associated with various traces of the bendable sensor at a periodic rate. For instance, the microprocessor 601 may be configured to monitor the state of each capsule individually, or each row of capsules, or each sheet of capsules to determine. This monitoring may occur at certain specified intervals. In some cases, in order to improve battery life, the monitoring may only be performed at longer intervals (e.g., every hour or every day) as opposed to shorter intervals (e.g., every minute or every five minutes). Thus, depending on which interval is chosen, the microprocessor 601 may determine, within the interval window, whether those capsules have been opened.

During this monitoring to determine whether capsules have been opened, the microprocessor 601 may also determine where the container was when it was opened. A GPS radio, WiFi radio, or other radio may be used to determine the location of the container. As such, the microprocessor 601 may determine whether a given container has been opened, when the container was opened, and where the container was when the container was opened. The microprocessor 601 may also note which type of usage occurred (including indicating whether the lid 608 was fully opened, partially opened, or not opened and, if partially opened, how far it was opened. If the lid was moved on multiple locations, the microprocessor 601 may note each type of movement and when it occurred.

As shown in FIG. 6, the system 600 may include a microphone 615 and a camera 616 communicatively connected to the microprocessor 601. The microphone 615 may be configured to capture sounds around the system 600 including a user's voice. The camera 616 may be configured to capture video, perhaps of the user of the system 600. For example, the display 606 may show a video of a patient's doctor or nurse or pharmacist describing how to use a given medication or explaining when to take the medication. Upon viewing the video, the patient may take the medication and then record a voice message or video for the caregiver. The patient's reply audio or video message may indicate that the patient has taken their medication. This audio or video recording may then be sent to appropriate caregivers in a secure, encrypted manner. The data associated with the audio/video recording may be transmitted using the transmitter/receiver 605.

Thus, a patient may be instructed using pre-recorded or live-streamed videos provided by a caregiver or other user. The patient may then use the system 600 to reply to that video using the provided microphone 615 and camera 616. The caregiver may then look at the audio/video recording and compare it to when the system 600 recorded an opening of a container. If the two match (within a specified degree of certainty), then the caregiver may relax knowing the medication was most likely taken. If the audio/video recording indicates, however, that the medication was taken and the microprocessor 601 has not registered a container 609 being opened, then the caregiver may be wary that the patient is not taking their medication as prescribed.

In addition to videos, the display 606 may be configured to display various images, words, symbols, or other means of communication. In some cases, the display 606 may include an interactive interface (e.g., a touchscreen) that is configured to present a question to the patient asking if the patient is experiencing various negative side effects or is having any other issues with the medication. If so, the patient's doctor may take certain actions with respect to the patient's prescription including telling the patient to take less of the medication and may further indicate that if the patient does not take less of the medication (or take it at a slower rate), the patient may forfeit their right to receive further medication.

Figure 7:
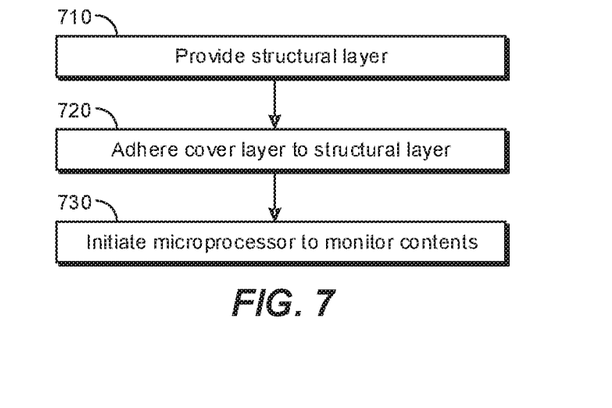
FIG. 7 illustrates a method of manufacturing an apparatus for tracking usage of an item.

Turning now to FIG. 7, a method of manufacturing 700 may be provided. The method of manufacturing 700 may include providing, at step 710, a structural layer (e.g. 620) to which a microprocessor 601 and a power source 604 may be coupled. The structural layer 620 may include a container 609 that is configured to hold at least one item. The container may include an opening 608 that allows access to the item. The method of manufacturing 700 may also include adhering, at step 720, a cover layer 621 to the structural layer 620. The cover layer 620 may be configured to cover the opening of the container 609. The cover layer 620 may include at least one bendable sensor 607 placed over the opening 608 of the container. The microprocessor 601 may be configured to determine, at step 730, using detected movements in the bendable sensor 607, whether the container has been opened.

Using this method of manufacturing, a manufacturer may be able to create an apparatus or system such as 100 of FIG. 1 or 600 of FIG. 6. In some cases, the method of manufacturing may include applying multiple layers including, for example, a blister layer, a blister lidding, a lidding foil, a sensor lidding foil, a dielectric layer, a sensor layer, and a backing layer. Each of these layers may be bonded together using heat, using glue, or using other bonding materials. Bendable sensors may be applied using printed traces or other types of traces. The printable traces may be applied using a material that is configured to bend and still remain intact, such that current or voltage may still flow through the traces, even after the lid coverings have been removed.

Accordingly, a tracking apparatus is described herein for tracking the usage of items including controlled substance items. The tracking apparatus makes use of bendable sensors that continue to register a resistance level or current flow even after a capsule has been punctured. This bendable sensor may be manufactured in a single layer that may result in fewer costs, fewer failures, and may be less subject to dirt or moisture. The overall system or apparatus may thus be more affordable, more useful and more reliable.

The concepts and features described herein may be embodied in other specific forms without departing from their spirit or descriptive characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

We claim:

1. An apparatus for tracking usage of an item, comprising:
a microprocessor;
a power source;
a structural layer to which the microprocessor and power source are coupled, the structural layer including at least one container that is configured to hold at least one item, the container including an opening that allows access to the item; and
at least one cover layer configured to cover the opening of the container, the cover layer including at least one bendable sensor placed over the opening of the container,
wherein the structural layer comprises a backing layer, wherein the cover layer includes a lidding foil and a sensor lidding foil, and wherein the apparatus further includes a blister layer, a blister lidding, a dielectric layer, and a sensor layer, and
wherein the microprocessor is configured to determine, using detected movements in the bendable sensor, whether the container has been opened.

2. The apparatus of claim 1, further comprising a transmitter configured to transmit data from the apparatus to a target destination.

3. The apparatus of claim 1, wherein the at least one container of the structural layer comprises a plurality of capsules for storing items, each capsule having its own opening and a bendable sensor extending over at least a portion of the opening.

4. The apparatus of claim 1, wherein the bendable sensor includes one or more traces.

5. The apparatus of claim 4, wherein the traces are generated and applied using printable ink.

6. The apparatus of claim 4, wherein the traces of the bendable sensors remain intact even when the at least one container of the structural layer has been opened.

7. The apparatus of claim 6, wherein at least some portion of current flows through the bendable sensor even after the at least one container has been opened.

8. The apparatus of claim 1, wherein the microprocessor determines whether the container has been opened using detected movements in the bendable sensor by detecting changes in at least one of capacitance, resistance, current, or voltage through the bendable sensor.

9. The apparatus of claim 8, wherein the changes in at least one of capacitance, resistance, current, or voltage through the bendable sensor are detected by the microprocessor without breaking the bendable sensor, such that the detected changes in capacitance, resistance, current, or voltage are non-zero values.

10. A system for tracking usage of an item, comprising:
a microprocessor;
a power source;
a structural layer to which the microprocessor and power source are coupled, the structural layer including at least one container that is configured to hold at least one item, the container including an opening that allows access to the item; and
at least one cover layer configured to cover the opening of the container, the cover layer including at least one bendable sensor placed over the opening of the container,
wherein the structural layer comprises a backing layer, wherein the cover layer includes a lidding foil and a sensor lidding foil, and wherein the system further includes a blister layer, a blister lidding, a dielectric layer, and a sensor layer, and
wherein the microprocessor is configured to determine, using detected movements in the bendable sensor, whether the container has been opened.

11. The system of claim 10, wherein the structural layer and the cover layer are combined into a single layer.

12. The system of claim 10, wherein the at least one bendable sensor comprises one or more ink traces.

13. The system of claim 10, wherein the microprocessor is configured to continually monitor a state associated with one or more traces of the bendable sensor at a periodic rate.

14. The system of claim 10, wherein the microprocessor is configured to determine whether the container has been opened, when the container was opened, and where the container was when the container was opened.

15. The system of claim 10, wherein the structural layer includes a plurality of containers, and wherein the microprocessor is configured to determine if a specified container is opened, even out of order in relation to other containers of the plurality of containers.

16. The system of claim 10, further comprising a camera and microphone communicatively connected to the microprocessor.

17. The system of claim 10, further comprising a display configured to display one or more images, words, or videos.

18. The system of claim 17, wherein the display comprises an interactive interface that is configured to present a question to a patient asking if the patient is experiencing one or more specified negative side effects.

19. A method of manufacturing, comprising:
providing a structural layer to which a microprocessor and a power source are coupled, the structural layer including at least one container that is configured to hold at least one item, the container including an opening that allows access to the item; and
adhering at least one cover layer to the structural layer, the cover layer being configured to cover the opening of the container, the cover layer including at least one bendable sensor placed over the opening of the container, wherein the structural layer comprises a backing layer, wherein the cover layer includes a lidding foil and a sensor lidding foil, and wherein a blister layer, a blister lidding, a dielectric layer, and a sensor layer are further provided, and wherein the microprocessor is configured to determine, using detected movements in the bendable sensor, whether the container has been opened.

\* \* \* \* \*